US006682940B2

(12) United States Patent
Pankowsky

(10) Patent No.: US 6,682,940 B2
(45) Date of Patent: Jan. 27, 2004

(54) PRODUCTS AND METHODS FOR SINGLE PARAMETER AND MULTIPARAMETER PHENOTYPING OF CELLS

(76) Inventor: Dan A. Pankowsky, 6030 Bresslyn Rd., Nashville, TN (US) 37205

( * ) Notice: Subject to any disclaimer, the term of this patent is extended or adjusted under 35 U.S.C. 154(b) by 0 days.

(21) Appl. No.: 09/909,677

(22) Filed: Jul. 20, 2001

(65) Prior Publication Data

US 2001/0041343 A1 Nov. 15, 2001

Related U.S. Application Data

(63) Continuation-in-part of application No. 09/563,564, filed on May 3, 2000.
(60) Provisional application No. 60/132,395, filed on May 4, 1999.

(51) Int. Cl.[7] .......................... G01N 33/553; G01N 1/00
(52) U.S. Cl. ........................ 436/176; 435/2; 435/7.21; 435/7.23; 435/7.24; 435/7.5; 435/7.94; 435/961; 436/518; 436/523; 436/524; 436/526; 436/527; 436/528; 436/538; 436/540; 436/824; 436/174; 436/175; 436/176; 436/177; 436/178
(58) Field of Search .......................... 435/2, 7.1, 7.2, 435/7.23, 7.24, 7.25, 7.5, 7.8, 7.94, 40, 52, 174, 181, 961; 436/513, 288.3, 518, 174, 523, 175, 526, 176, 524, 177, 538, 178, 540, 527, 824, 528, 828; 422/101

(56) References Cited

U.S. PATENT DOCUMENTS

| | | |
|---|---|---|
| 4,554,101 A | 11/1985 | Hopp |
| 4,659,678 A | 4/1987 | Forrest et al. |
| 4,794,077 A | 12/1988 | Busch et al. |
| 5,047,507 A | 9/1991 | Buchegger et al. |
| 5,087,557 A | 2/1992 | McClure |
| 5,095,097 A | 3/1992 | Hermentin et al. |
| 5,173,399 A | 12/1992 | Mehta et al. |

(List continued on next page.)

FOREIGN PATENT DOCUMENTS

| | | | |
|---|---|---|---|
| EP | 016 552 A1 | 10/1980 | |
| EP | 0 616 836 A | 9/1994 | |
| EP | 0 749 580 | 4/2000 | ................. 436/526 |
| WO | WO 97/36004 | 2/1997 | ................. 435/7.23 |
| WO | WO 98/28622 | 7/1998 | ................. 436/526 |

OTHER PUBLICATIONS

Weltzien R B, Visualization of beta–amyloid peptide (Abeta) phagocytosis by human mononuclear phagocytes: dependency on Abeta aggregate size. Journal of Neuroscience Research, (Feb. 15, 2000) 59 (4) 522–7 (Abstract).*
Esteban M A; Methodological aspects of assessing phagocytosis of *Vibrio anguillarum* by leucocytes of gilthead seabream (*Sparus aurata L.*) by flow cytometry and electron microscopy. Cell and Tissue Research, (Jul. 1998) 293 (1) 133–41 (Abstract).*

(List continued on next page.)

*Primary Examiner*—Long V. Le
*Assistant Examiner*—Gailene R. Gabel
(74) *Attorney, Agent, or Firm*—Pearne & Gordon LLP

(57) ABSTRACT

A method of single parameter and multiparameter characterizing of cells, particularly immunophenotyping of cells, is provided. The method preferably uses antibody-coated microspheres which are adapted to bind to specific types of cells. One or more sets of coated microspheres are contacted simultaneously or sequentially with a suspension of cells and bind the cells they are adapted to bind to form bead-cell complexes. Cells may bind to one or more microspheres. The bead-cell complexes are then separated from the suspension The complexes are preferably stained and then examined to characterize the cells, preferably the cells bound to the microspheres. A method of quantitating a specific cell type is provided. A kit and apparatus for performing the method are also provided.

20 Claims, 1 Drawing Sheet

U.S. PATENT DOCUMENTS

| | | |
|---|---|---|
| 5,231,005 A | 7/1993 | Russell et al. |
| 5,256,532 A | 10/1993 | Melnicoff et al. |
| 5,260,192 A | 11/1993 | Russell et al. |
| 5,298,426 A | 3/1994 | Inami et al. ............ 436/63 |
| 5,338,689 A | 8/1994 | Yves et al. |
| 5,340,719 A | 8/1994 | Hajek et al. |
| 5,348,859 A | 9/1994 | Brunhouse et al. |
| 5,366,866 A | 11/1994 | Xu et al. |
| 5,374,531 A * | 12/1994 | Jensen ................ 435/7.24 |
| 5,426,029 A | 6/1995 | Rittershaus et al. |
| 5,460,940 A | 10/1995 | Yves et al. |
| 5,501,949 A | 3/1996 | Marshall |
| 5,512,432 A | 4/1996 | Lapierre et al. |
| 5,554,505 A | 9/1996 | Hajek et al. |
| 5,667,966 A | 9/1997 | Paul et al. |
| 5,716,787 A | 2/1998 | Dunn et al. |
| 5,759,864 A | 6/1998 | Cushing et al. |
| 5,776,711 A | 7/1998 | Vyas et al. |
| 5,800,983 A | 9/1998 | Bridon et al. |
| 5,830,636 A | 11/1998 | Paul et al. |
| 5,843,450 A | 12/1998 | Dawson et al. |
| 5,846,751 A | 12/1998 | Pronovost et al. |
| 5,858,682 A | 1/1999 | Gruenwald et al. |
| 5,863,802 A | 1/1999 | Yves et al. |
| 5,948,627 A | 9/1999 | Lee et al. |
| 5,981,180 A | 11/1999 | Chandler et al. ............ 435/6 |
| 6,184,043 B1 | 2/2001 | Fodstad et al. ............ 436/526 |
| 6,221,579 B1 * | 4/2001 | Everhart et al. ............ 435/5 |
| 6,265,229 B1 * | 7/2001 | Fodstad et al. ............ 436/526 |

OTHER PUBLICATIONS

Pronai L; Enhanced superoxide generation and the decreased superoxide scavenging activity of peripheral blood leukocytes in Behcet's disease—effects of colchicine. Clinical and Experimental Rheumatology, (May–Jun. 1991) 9 (3) 227–33 (Abstract).*

Juliano C; Action of anticytoskeletal compounds on in vitro cytopathic effect, phagocytosis, and adhesiveness of *Trichomonas vaginalis*. Genitourinary Medicine, (Aug. 1987) 63 (4) 256–63 (Abstract).*

Band A H; Mechanism of phagocytosis of mycobacteria by Schwann cells and their comparison with macrophages. International Journal of Leprosy and Other Mycobacterial Diseases, (Jun. 1986) 54 (2) 294–9 (Abstract).*

Rye et al., *Immunobead Filtration: A Novel Approach for the Isolation and Propagation of Tumor Cells*, American Journal of Pathology, vol. 150, No. 1, Jan. 1997, pp. 99–106.

* cited by examiner

PRODUCTS AND METHODS FOR SINGLE PARAMETER AND MULTIPARAMETER PHENOTYPING OF CELLS

This application is a continuation-in-part of U.S. patent application Ser. No. 09/563,564 filed May 3, 2000. This application claims the benefit of U.S. Provisional Application Serial No. 60/132,395 filed May 4, 1999. The contents of application Ser. Nos. 09/563,564 and 60/132,395 are incorporated herein by reference in their entirety.

FIELD OF THE INVENTION

The present invention relates generally to phenotyping and immunophenotyping of cells and more particularly to single parameter and multiparameter phenotyping and immunophenotyping of cells.

BACKGROUND OF THE INVENTION

Immunophenotyping of cells and tumors, particularly hematopoietic tumors, is often of critical importance for clinical evaluation of cancer patients. However, currently available methodologies, particularly flow cytometry, are expensive and require a high degree of suspicion at the time of biopsy. All too often, even before the diagnosis of cancer is made, precious tissue must be set aside for possible immunophenotyping. If tissue is not set aside and there is cancer present, the correct subtyping of the tumor (and proper assignment to treatment protocols) cannot be done after the fact. Methods that do not require forethought, such as immunostaining of paraffin blocks, are far less sensitive and do not work well in laboratories that do not perform these stains frequently. Flow cytometry is the currently accepted "gold standard" for immunophenotyping of hematopoietic cell types. However, there are several problems with the method. The expense of establishing and maintaining these laboratories is perhaps the most severe problem. Generally large hospitals, academic centers, or commercial reference laboratories are the only institutions capable of establishing flow cytometry laboratories. These laboratories often charge a premium for their services, and transportation of specimens to laboratories is not a trivial problem. Since flow cytometry requires live cells, specimens must be handled under sterile conditions. In laboratories where the technology is unavailable, a fresh specimen has to be prepared and shipped to a flow cytometry laboratory under sterile conditions for evaluation. Uncontrollable factors such as temperature variations, rough handling, bacterial contamination, or shipping delays may render samples unsuitable for analysis. In addition, flow cytometry requires technologists who have specialized training and their time must often be dedicated solely to the technology itself, further increasing the expense of the procedure. Relatively large volumes of cells must be analyzed in order to obtain statistically meaningful results during analysis. In addition, red cells must be removed from the sample prior to analysis. This is because the number of red cells in blood and bone marrow samples is far greater than other cells types, and shear numbers alone would overwhelm the sensitive detectors of the machines. The sample preparation method therefore requires Ficoll-Hypaque separation, followed by multiple washes, followed by a lysis step to lyse remaining red cells. This method virtually eliminates megakaryocytes from most analysis and frequently destroys delicate malignant cells (particularly from the relatively common tumors such as large cell lymphoma and Hodgkin's disease). It is in these situations that the great sensitivity and complexity of flow cytometry may work to its disadvantage.

Despite the problems described above, however, flow cytometry can very accurately and with great sensitivity identify the presence of malignant cells and characterize the kind of malignant cells. Without the information that flow cytometry provides, cases can be frequently incorrectly diagnosed with catastrophic consequences for the patient. This is particularly true in the setting of a type of biopsy called fine needle aspiration where examination of a slide alone by light microscopy may be quite difficult.

What would be very useful to the average hospital pathologist or to any physician in an outpatient or remote setting is a device or kit that would allow the same kind of single parameter or multiparameter analysis of samples using cheaper, more readily available materials. This would eliminate the need for specialized laboratories and technologists dedicated solely to the flow cytometry technology itself and would allow any well trained clinical laboratorian ready access to the same kind of analysis. Furthermore, if the need for live cells could be eliminated, cells could be preserved by appropriate fixatives which would broaden the availability of immunophenotyping data.

Over the last 20 years there has been a tremendous growth in the identification and characterization of molecules expressed by blood cells on their cell membranes (called cell surface antigens). This growth in understanding has been accompanied by the refinement of technologies that allow the rapid and sensitive identification of these molecules on the surfaces of live cells. However, the overwhelming majority of these cell surface antigens are not unique to one type of cell. There is only rarely a single diagnostic marker to identify a cell type. Instead, most cell populations must be characterizing by analyzing multiple parameters at the same time.

Antibodies are proteins produced by the body's immune system that have the property that they bind to a single site on a specific molecule (referred to as an antigen). Antigen-antibody complexes are formed when an antibody binds its respective antigen. Normally, these complexes are then cleared by the immune system to rid the body of an infection. However, the immune system has a virtually limitless capacity to produce unique antibodies, which can be tailored to identify particular substances, even when present in very small quantities. Antibodies are now commercially produced to literally hundreds of different antigens. Furthermore, antibodies can be easily tagged with marker molecules, such as fluorescent molecules, dyes, or other substances that make identifying the presence of an antigen-antibody complex a relatively simple matter. This well-known biochemical reaction has been used to develop a methodology called flow cytometry. In flow cytometry, intact cells are treated with antibodies that bind specific markers on the cell surface. The antibodies are, in turn, labeled with a fluorescent molecule and the cell suspension then flows past a light beam with a light detector which counts the number of fluorescent cells versus the other cells present. This technology has proved tremendously useful in identifying malignant cell populations in blood and tissue samples from patients.

In flow cytometry, a cell suspension is treated with antibodies labeled with fluorescent molecules (fluorochromes), washed, and placed in the machine. The cell suspension is "focused" using buffer solutions so that the cells pass through the flow detector in a single file. When each cell passes through the flow detector, a beam of laser light is passed through the cell. Some of the light passes through the cell (called forward light scatter) and some is refracted at an angle (called side scatter). Forward scatter increases with a cell's size and side scatter increases with a cell's internal complexity (mostly granules within the cytoplasm). Thus using just these two measurements, individual cell types can be roughly categorized. However, there are also light detectors, which, by using appropriate color filters, can specifically detect the fluorescence given off by the antibodies that are attached to the cell surface. Since current state of the art machines have up to four different color detectors (referred to as four-color flow cytometry), up to four different antibodies can be added to the same tube. Samples from individual patients are usually divided into multiple tubes, each of which contains multiple antibodies. Data analysis is therefore quite complex, and requires computers that are capable of simultaneously displaying multiple plots from each tube. This is referred to as multiparameter analysis. This simultaneous analysis of multiple parameters is necessary to first electronically isolate and then characterize cell populations. Therefore, even though modem flow cytometers analyze up to 6 simultaneous parameters (forward scatter, side scatter, and four antibodies) 3 of the parameters must be used for electronic isolation of cell types (forward scatter, side scatter, and CD45 staining intensity). Broad categories of cells present in hematologic samples are known in the art and include myeloid cells, monocytes, lymphocytes, megakaryocytes, and red cells. In other words, these 3 parameters must be used to roughly mimic what the human eye does so effortlessly: identify or characterize broad categories of cells. Indeed, laboratories commonly hire technicians with 2 years of training (only part of which is in the area of hematology) who can, with a very reasonable degree of accuracy and precision, identify or characterize different cell types present in blood samples. With some additional training, they can also correctly enumerate cell types within bone marrow aspirate samples. Thus if the human eye were also equipped with the means to also identify cell surface antigens, there would be no need for flow cytometry for this purpose. Furthermore, of the remaining 3 parameters available for analysis on the flow cytometry, only 2 can be displayed in any one plot although new software exists that can display 3 dimensional plots. While 3 dimensional plots add to convenience and are applicable in limited situations, two parameter analysis is quite sufficient in most cases. This last point is critical, since any method that seeks to supplant flow cytometry must have the ability to characterize at least 2 cell surface markers simultaneously.

Analysis of cell populations by flow cytometry is not a trivial process and requires highly trained personnel as outlined above. Both single parameter and multiparameter analysis can be performed. If data is analyzed as histogram plots of fluorescence of a single marker versus cell number, then one parameter analysis is being performed. Analyzing two such histograms of a single gated cell population could then be referred to as simultaneous single parameter analysis. An example of simultaneous single parameter analysis would involve the use of such plots to identify cell surface expression of both the B-cell marker CD20 and the light chain kappa. Analysis of the binding of each set of antibodies is independent of the other. In multiparameter analysis, the binding of the two antibodies are linked and are not independent. Analytical methods require the binding of both antibodies simultaneously brought together in a single histogram such as fluorescence 1 versus fluorescence 2. Characterization of the target cell population is best performed by analysis of this fluorescence 1 vs. fluorescence 2 plot and analyzing the binding characteristics of each of these antibodies together. This decreases the possibility of an error that would incorrectly analyze two overlapping cell populations as a single cell population.

Finally, with the limited exception of DNA ploidy analysis, characterization of solid tumors and non-hematopoietic tumors is quite limited by flow cytometry. Often there are not well developed protocols for developing cell suspensions. In addition, tumor cells may be delicate and may not survive processing. In addition, many markers used for solid tumors such as vimentin or smooth muscle actin are intracytoplasmic antigens and may be difficult to assay by flow cytometry. In addition, most available markers for these other tumors are not specific markers for the tumors and many normal cells, including cells present in the background of the available sample, may be strongly positive for the same markers. Therefore, interpretation of these kinds of samples without specific morphologic correlation is hazardous at best.

An object of the invention is to provide a cheaper, more accessible method for single parameter and multiparameter analysis of cell populations. This analysis is not limited to just cell surface markers but also optionally includes identifying active receptor sites on cell surfaces, loss of cell surface proteins, intracellular proteins, and intracellular nucleic acid sequences. One of the features of this invention is that the target cell population is being analyzed by preserving morphologic characteristics of the cells for analysis. In addition, it is also possible to count events to obtain specific cell numbers in relation to specific sample volume.

SUMMARY OF THE INVENTION

A method of characterizing cells comprising the steps of: a) providing a suspension of cells in a liquid medium, said cells including first cells, b) contacting a group of first beads with said suspension, each of said first beads being coated with a binding substance or being magnetic such that each first bead is adapted to bind to at least one of said first cells, c) incubating said first beads with said suspension for a period of time effective to permit said first cells to bind to said first beads to form first bead-first cell complexes, each first bead-first cell complex comprising a first bead and a first cell, d) separating said first bead-first cell complexes from said suspension, and e) examining said separated first bead-first cell complexes and characterizing said first cells. A method of quantitating a specific cell type in a cell suspension is also provided which comprises the steps of providing a suspension of cells in a liquid medium, counting the number of certain cells per unit volume of the suspension, incubating the suspension in beads, estimating the relative percentages of certain cells bound to beads, and calculating the number of certain cells per unit volume of the suspension. A method for preparing an enriched population of a target cell is also provided, which includes the step of separating first bead-target cell complexes from a suspension and resuspending the target cells in another liquid medium.

DETAILED DESCRIPTION OF THE PREFERRED EMBODIMENTS OF THE INVENTION

Figure 1:
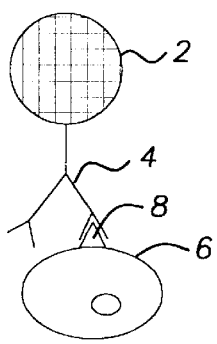
FIG. 1 is a schematic illustration showing a cell bound to an antibody which is bound to or coated on a bead.

As used herein, when a preferred range such as 5–25 is given, this means preferably at least 5 and, separately and independently, preferably not more than 25. The cells herein are preferably human cells. If a first group of cells does not include members of a second group of cells, and the second group of cells does not include members of the first group of cells, the two groups do not overlap. "Visually distinguishable" includes visually distinguishable via light microscopy. Quantitate includes to estimate or enumerate or count the number of. Phenotyping includes immunophenotyping and genotyping.

The invention uses beads. As used herein, beads means small particles or support surfaces, preferably microspheres, more preferably plastic microspheres, more preferably polystyrene microspheres (also referred to as latex beads or spheres or microspheres), which have preferably been coated with a binding substance or which are magnetic. As used in the claims, "first beads" includes beads which have been coated with a binding substance or which are magnetic. The bead may be any solid support surface or particle that can be suspended in an appropriate solution. Preferred beads are available as polystyrene microspheres from Bangs Laboratories, Fishers, Ind. The bead sizes are preferably greater than 5 microns diameter, preferably 5.5–10.3 microns, less preferably at least 5.5 or 10 or 12 microns and preferably not more than 12, 15, 20 or 30 microns diameter, far less preferably less than 5 microns, such as at least 1, 2 or 3 microns diameter. 5.5 and 10.3 micron beads are preferred. The beads can also be colored, such as red or blue, less preferably green, purple, orange, brown, yellow, or any other color. The beads are preferably coated with a binding substance, such as antibodies or immunoreactive proteins, or any molecule that can bind to, or interact with a cell surface in such a way as to bring the cell and the bead into contact or adherence with each other or to bind with each other; alternatively, the bead can contact or bind with the cell surface through electrostatic charge interactions or magnetic interaction; all of these concepts being covered by the terms "binding to" or "bind to". When a bead binds to a cell, it forms a bead-cell complex. In the invention the cell-bead interaction forms a large enough complex to inhibit the passage through a filter containing pores of appropriate dimensions. The filters are preferably sized and selected such that unbound cells and beads will pass through the pores but bound cell-beads do not. These complexes are then transferred to a glass slide and stained with a variety of stains so as to render the complexes visible by routine microscopy. The complexes and cells are examined and the cells are characterized. Examples of binding substances or reactive substances that may be used to coat the bead surface include, but are not limited to: antibodies to specific cell surface proteins, small molecules that bind receptors or other cell surface molecules such as IL-2 or GM-CSF, avidin, biotin, or beads may remain uncoated in suspension that can interact by other means with cells. The antibodies that can be used are those known in the art. Many such antibodies are available from commercial companies, such as Zymed Inc., South San Francisco, Calif. and Dako Corp., Carpinteria, Calif.

Beads or microspheres can be made from a variety of substances including gold, ferritin, polyacrylamide, or polystyrene. The latter is among the preferred substances as beads can be made precisely to any size specification and can be uniformly conjugated to both molecular linker arms and reactive binding substances. Polystyrene microspheres (also known as "latex microspheres") may be prepared by methods known in the art which are incorporated by reference herein. Binding substances that can be used include monoclonal antibodies, polyclonal antibodies, antibody "cocktail" mixtures, antibody fragments (such as Fc portions or Fab or Fab' fragments in either monovalent or divalent forms), small molecules that bind specific cell surface receptors, covalent and non-covalent linkers, and indirect adherence such as utilizing electrostatic or magnetic or paramagnetic attraction.

The prior art includes U.S. Pat. Nos. 5,554,505; 5,348,859; 5,340,719; 5,231,005; 5,260,192; 5,338,689; 5,256,532; and 5,501,949, the entire contents of which are incorporated herein by reference. These patents include discussions of using certain microspheres or beads for identification of cells. It is known in the art how to provide a suspension of cells in a liquid medium for analysis.

A second feature of a preferred embodiment of the present invention is that it concentrates cells by using an appropriate filter without added manipulation of the cell suspension by cell lysis or added incubation steps of submicroscopic paramagnetic microspheres. The filters to be used in the invention can be any of those known in the art, such as gynecological filters from Cytec Corp., Boxborough, Mass. The filters preferably have a pore size larger than the beads being used so that all or most or substantial amounts of unbound beads and unbound cells pass through, but the pore size is preferably small enough so that all or most or substantial amounts of beads bound to cells are trapped on the filter, such as the filter pore size being about 1, 2, 3, 4, 5, 6, 8, 10 or 12 microns larger than the bead size. Preferred filter pore sizes include 10–15, less preferably 7–20, 7–30 or 7–40 micron pore sizes. Alternatively the filter pore sizes can be at least 15 or 20 microns. The filter is preferably mounted on a solid support, such as at the end of a tube through which the suspension can drain.

Other filtration methods can also be used. These filters include any solid support that preferentially allows cell-bead complexes or individual cells or beads below a given size to pass through the filter while those above a given size remain trapped in the filter. Other filter types that can be used include columns of solid materials such as sepharose which contain a well-defined average pore size. Such columns are known in the art. Another technique which can be used is to fix coated beads using techniques known in the art to any solid support such as a glass slide or a plastic substrate, such as an opaque plastic substrate. The cell suspension is then incubated on the slide (or substrate) or the slide (or substrate) is incubated in the cell suspension. In this way the beads are contacted with the suspension. The target cells adhere to the beads. Optionally a second and third or more bead type can be affixed to the cells as described herein to make larger bead-cell complexes. The suspension is then drained off the glass slide or substrate. In this way the bead-cell complexes are separated from the suspension. If a glass slide was used, visualization can then be done. If some other substrate was used (for example, opaque plastic) the beads can then be released from the substrate or support and the bead-cell complexes can be affixed to a glass slide for examination.

A cell suspension is preferably prepared from a peripheral blood sample, a bone marrow aspirate, a fine needle aspirate, a lymph node biopsy, or a body site specimen. In the method described herein, single parameter, simultaneous single parameter, and true multiparameter analysis is possible which compares to the level of sophistication of analysis possible by flow cytometry. Beads that can be easily distinguished from each other optically either by size, color, or both can be added to a cell suspension either simultaneously or sequentially. Positive binding by the target cell population results in a bead-cell complex that has a significantly larger physical size than either unbound cells or beads. These complexes can be then easily concentrated and separated from the rest of the solution using an appropriately sized filter containing pores of sufficient size to let unbound cells and beads to pass through while complexes remain on the filter. The method may also be used in reverse, in that abnormal cell populations may fail to bind beads while normal cells bind strongly. An example of this latter method can be found with the myelodysplastic disorders (MDS), which currently cannot be diagnosed by flow cytometry with any degree of reliability. Normal human myeloid cells strongly express surface markers such as CD11b, CD13, CD15, CD16 and CD33. However, in MDS, these cell populations lose expression of these markers. However, as normal cells degenerate from prolonged storage or poor specimen handling such as temperature extremes, which may occur in specimen transport, they also lose expression of these markers. Flow cytometry cannot distinguish between these two conditions. However, degenerated cells are easily recognized morphologically from the dysplastic cells of MDS. Loss of binding by beads coated with antibodies to these markers could easily be identified (with a slide made of the cells passing through the filter as well as those trapped on the filter). Therefore, this method may be used to diagnose MDS, heretofore only diagnosable in those minority of cases showing abnormal cytogenetics or persistent hematologic abnormalities after prolonged clinical follow up. As an example of MDS analysis, one can look at a peripheral smear. If the cells are degenerated, get a new sample. If the cells are not degenerated, incubate the cell suspension with large beads coated with anti-CD13. Then add small beads coated with anti-CD15 and let react. Then filter (can be small pore size to trap both bound and unbound cells, or large pore size to trap bound cells only, in which case unbound cells are collected from what went through the filter). If the result is many complexes such as those depicted in FIG. 3 and few unbound cells, this indicates normal cells. If there are few bound cells and many unbound cells, this suggests MDS. Immature cells also have weak binding, but this can be seen morphologically. The same procedure can be done with CD11b and CD16.

One can also count beads trapped on the filter prior to transfer to the glass slide. Using methods such as light scattering, reflectance, fluorescence, or electrostatic field changes, the number of beads trapped on the filter can be counted. An average number of cells bound to each bead can be obtained and an estimate of the number of cells in the original sample volume obtained.

Figure 2:
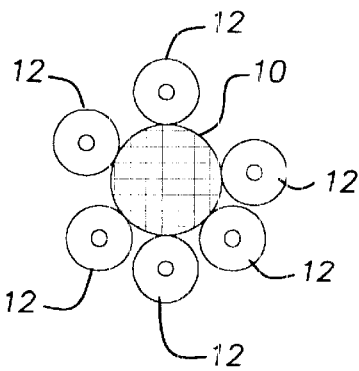
FIG. 2 is a schematic illustration showing a number of cells bound to a bead.

With reference to FIG. 1 there is shown, not to scale, a bead 2, such as a polystyrene microsphere, which has coated thereon and bound thereto a binding substance 4 such as an antibody. There is also a cell 6, such as a target cell, which has a cell surface marker 8. The binding substance 4 or antibody binds to the cell surface marker 8 on the target cell 6. FIG. 2 illustrates how this kind of reaction may appear on a glass slide; a group of cells or target cells 12 have bound to a bead 10. This shows single parameter binding of cells to beads. The ratio of beads to cells should be adjusted properly for effective results. The actual number of cells binding the bead is variable, ranging from a single cell to numerous cells crowding the bead's surface.

Figure 3:
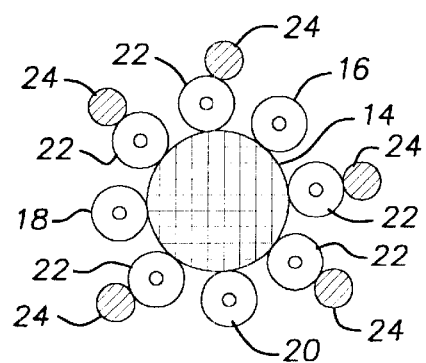
FIG. 3 is a schematic illustration showing a number of cells bound to a bead in the center, and five smaller beads bound to five of the cells.

With reference to FIG. 3 there is shown a large bead 14 coated with a binding substance which has bound to eight cells 16, 18, 20, 22. Small beads or different colored beads 24 coated with a different binding substance have bound to the cells 22 but not to the cells 16, 18, 20. This provides positive identification of target cells 22. This illustrates multiparameter analysis. Cells 22 is a subset of cells 16, 18, 20, 22. A variable number of beads 24 can bind to each cell 22. In some cases each cell bound to bead 14 will be bound to one or more beads 24, or each cell bound to bead 14 may be unbound to small beads. Note that different kinds of cells may bind to the large bead 14 that can in some cases be distinguished morphologically. Preferably the large bead 14 is added first to the cell suspension so that a plurality of cells can bind to its surface. Then the small beads 24 are added to bind to the periphery of the complex. Alternatively small beads 24 can be added first or small beads 24 and large beads 14 can be added simultaneously. The order of addition is dependent in large part upon the relative concentrations and surface areas of the beads and the cells. For example, you would not want to add beads 14 or 24 in such concentrations that they completely cover or obscure the surface area of the target cells and thus prevent access thereto by the other beads. Preferably there is an excess of target cells to fully coat the bead. Optionally the suspension can be filtered after the first complex is formed, to trap the first complex and resuspend it before the second beads are added. Thus a group of complexes can be filtered and resuspended before a subsequent set of beads is added; this can lead to more certain and distinct results by removing materials which would provide interference. The beads may be distinguishable in size or color or both. Further levels of multiparameter analysis can also be carried out, such as by adding to FIG. 3 another set of different sized or different colored beads which would bind to a first subset of cells 22 but not the remaining cells 22, thus providing positive identification of said first subset of cells 22. In this manner subsequent or additional levels of multiparameter analysis can be carried out.

There is a wide variety of available beads that can be used, and those selected would depend on the specific application. In multiparameter analysis beads that can be easily distinguished by either size or color are preferable. For example, two sets of colorless beads sized 10 and 5 microns respectively can be used to isolate a population of B cells using 10 micron beads coated with an anti-pan B cell antigen such as CD19 and 5 micron beads coated with anti-kappa. Multiparameter analysis that cannot be easily mimicked by flow cytometry is available by a minor variation of this example. Colorless 10 micron beads are used to bind B cells by using anti-CD19 coated beads. 5-micron colorless beads are coated with anti-kappa while dark blue 5-micron beads are coated with anti-lambda. Similarly, a blast cell population can be analyzed using anti-CD34 coated 10 micron beads and anti-CD19 coated colorless 5 micron beads. Colored 5-micron beads coated with anti-CD13 are simultaneously added for rapid characterization of most blast cell populations.

Preferred Methods:

1) Substantially identical beads are purchased commercially precoated with strepavidin (Bangs Laboratories, Fishers, Ind.). A small quantity is suspended in any buffered salt solution such as phosphate buffered saline or commercially available antibody diluent. The beads are incubated with biotinylated goat anti-mouse antibodies for 30 minutes (however, any biotinylated anti-allogeneic antibody may be used). The suspension is centrifuged and the supernatant drawn off. The incubation is repeated two times to ensure coating of as much of the available surface area of the beads as possible. The beads are then washed three times using the same buffer. The suspension is then incubated with specific mouse anti-human antibodies for 1 hour (or any non-biotinylated anti-allogeneic antibody specific for the target cell population may be used). The suspension is again washed three times and diluted to the desired concentration. The resulting suspension can be refrigerated at 4 degrees Centigrade until use. Alternatively, biotinylated primary antibodies may be used without the use of secondary antibodies. The beads produced by this technique are substantially identical.

2) Beads are precoated with anti-Fc receptor antibodies (Bangs Laboratories, Fishers, Ind.) such as goat anti-mouse IgG Fc receptor antibodies. These beads can then be suspended in a solution of antibodies which would spontaneously bind to the anti-Fc receptor sites on the beads. In the example cited above, mouse anti-human antibodies would be bound to the beads followed by appropriate washing steps similar to that described above.

3) Binding substances such as any protein, peptide, or nucleotide sequence may be bound by other chemical or specific binding methods. For example, polystyrene microspheres are "naturally" left coated with sulfate surface groups after manufacture. These ligands can be used to link proteins and peptides directly to the surface of the beads. Examples of such functional surface groups that can be coated on the surface includes, but is not limited to, aldehyde, aliphatic amine, amide, aromatic amine, carboxylic acid, chloromethyl, epoxy, hydrazide, hydroxyl, sulfonate, and tosy (toluene sulfonyl) reactive ligands. These can then be used in turn to link peptides, proteins, oligonucleotides, and other biochemical ligands to the surface. These ligands or binding substances would in turn be used to bind specific sites on cell surfaces which would link the cell to the surface of the bead. For example, a small molecule such as the hormone IL-2 could be used by one of the above methods to coat beads with the intention of binding IL-2 receptor sites (CD25) on cell surfaces. This could be used to bind cells such as T-cells, monocytes, and neoplastic cells such as hairy cell leukemia.

Other Methods:

Submicroscopic paramagnetic microspheres (preferably less than 1 micron in diameter) are bound to any reactive biomarker of interest. The binding that is used could be any of the above methods. Cells are then permeabilized and fixed using a variety of detergents and weak fixative solutions such as 1% paraformaldehyde. Alternatively a number of commercially available permeabilizing kits are available for this purpose such as IntraStain (Dako Corp., Carpinteria, Calif.). The reactive biomarker, such as antimyeloperoxidase antibodies, anti-terminal deoxytidyl transferase antibodies, or specific RNA or DNA probes, is then incubated with the cell suspension. The biomarkers and paramagnetic particles get inside the cell and, for example, the probe binds to the intracellular target. The cells are then washed and resuspended in a suitable buffer such as PBS or RPMI. The suspension is then incubated with magnetic beads or microspheres of a size or color easily visualized, such as 1 to 20 or 3–15 or 5–10 or 10–20 microns. The magnetic beads bind to the cell surface, but cannot cross the membrane, to create a cell-bead complex that is easily trapped such as via filtration.

In one example, abnormal blasts in a bone marrow suspension can be permeabilized and incubated with anti-myeloperoxidase antibodies bound to submicroscopic paramagnetic microspheres. The suspension is then washed three times in buffered salt solution and resuspended and incubated with large magnetic beads of a preferred size of 5–15 micron diameter to create cells bound to large beads.

In another example, specific DNA sequences (probes) are bound to submicroscopic paramagnetic microspheres using methods such as avidinated microspheres and biotinylated probes. Cells from a patient with chronic myelogenous leukemia are permeabilized and incubated with probes binding to the specific bcr-abl translocation that is diagnostic for the disease. The suspension is then washed and incubated with large magnetic beads of a preferred size of 5–15 micron diameter to create cells bound to large beads.

Detection and Analysis:

The cell-bead complexes (cells bound to beads) provided or obtained as described above are then passed through a solid support filter having a porosity of sufficient size to allow unbound cells and beads to pass through. There are several acceptable filtration techniques such as porous columns and solid supports. In a preferred method, the suspension is passed through the filter using a variety of acceptable methods which includes gravity, suction (applied vacuum), positive pressure on the fluid side, or wicking the fluid through the filter using a porous absorbable material such as gauze pads. Various devices that can be used include pistons, syringes, or suction methods to create a negative pressure to pass fluid through the filter. In a preferred embodiment, a single solid filter with a pore size of 10–15 microns is used. Cell-bead complexes remain trapped on the filter and the layer is then transferred to a glass slide by direct contact with the slide and applying gentle pressure. The resulting slide preparation can be stained using a variety of commercially available stains such as hematoxylin and eosin, Papanicolau stain, or any Romanowsky stain. In a preferred embodiment, the cells remain suspended in a compatible buffer such as PBS, RPMI, or commercially available antibody diluent and the resulting slide is stained with Wright-Giemsa stain. Alternatively, cells may be suspended in ethanol or a commercially available fixative such as Cytolyte (Cytyc Corp., Boxborough, Mass.). The resulting slide is then stained with Papanicolau or hematoxylin and eosin stains. The complexes are examined and the cells are characterized under routine light microscopy.

The invention can be used to perform single parameter analysis correlated with morphology, simultaneous single parameter analysis, or multiparameter analysis. In single parameter analysis, (depicted in FIGS. 1 and 2) a single bead type is added to a suspension of cells in a liquid medium so that after filtration the slide is provided with an enriched single cell population. This is useful as a simple screen to determine if a cell population has a particular characteristic such as distinguishing monocytes from monocytoid B lymphocytes as cited in Example 1 below. In this configuration, cells bind to beads and are visible on the glass slide for analysis. Alternatively, a B cell population can be assayed for expression of kappa or lambda by using two separate slides or slide wells each of which contain a single bead type (anti-kappa or anti-lambda). Another variant of this analysis is to add simultaneously to the cell suspension two different bead types, one anti-kappa and a second anti-lambda. This is an example of simultaneous single parameter analysis since binding of each bead type is independent of the other but the results are analyzed together. An analogous situation occurs in flow cytometry analysis when fluorescence is displayed vs. cell number to obtain a single histogram. In kappa and lambda analysis, a monoclonal population can only be detected by simultaneous analysis of both histograms and looking for single peaks of fluorescence. Finally, multiparameter analysis can be performed by linking detection of two different characteristics so that analysis is performed together. In this case, binding of one set of beads occurs, followed by a second and optionally more sets of beads (see FIG. 3). Analysis looks for simultaneous binding of more than one set of beads to the target cell population (as depicted in Example 2 below).

The invention can be used to detect abnormal loss of binding when strong binding would be expected. For example, normal myeloid cells such as mature granulocytes and monocytes in the peripheral blood would be expected to strongly express the surface markers CD13, CD33, CD11b, and CD16. In a bone marrow sample there would be a continues range of increasing expression of these markers as the cell matures. However, cells showing abnormal maturation, as seen in myelodysplasia, would show diminished expression of these markers. This phenomenon has been previously described by Davis, et al. and can be seen in flow cytometry analysis as abnormal patterns of expression on appropriate histograms. However, a similar loss of expression is seen when normal cells die and degenerate as occurs in specimen mishandling or aging. Since morphologic correlation is less than optimal by flow cytometry, the phenomenon has limited diagnostic usefulness, particularly when the specimen has been transported long distances. In the present invention, cells can be visualized on the glass slide to confirm their viability. Normal cells would strongly bind beads coated with these markers but there would be decreased binding of beads in cells with myelodysplasia. In the low grade myelodysplasias such as refractory anemia and refractory anemia with ringed sideroblasts, there are often no objective diagnostic criteria for confirming the diagnosis. Current state of the art in such cases requires prolonged follow up and diagnosis by exclusion of other possible entities such as ethanol toxicity or megaloblastic anemia from vitamin B12 or folate deficiency. The invented method provides a much needed positive diagnostic test.

A complementary detection method is that prior to transfer of the cells to a glass slide, the filter is gently rinsed and scanned using a light beam of either a white light beam or a specific wavelength to correspond to the excitation wavelength of fluorescent beads. The number of events is counted electronically and the cells are then transferred to a glass slide and stained. The average number of cells per microsphere is then obtained manually and an estimate of the total number of target cells in the sample can be estimated (assuming that a known volume of sample is used).

Preferred Applications:

1) Single parameter analysis of tumors and other specific cell populations. A suspected tumor with a known immunophenotype can be analyzed to confirm the presence of a single marker as outlined in Examples 1 and 3 below. This is most useful in settings where a single issue regarding cell phenotype needs to be settled. In Example 1 below, knowing that the abnormal cell population is of B cell origin is sufficient information to proceed with further studies, since this suggests (but does not prove) malignancy. In Example 3 below, knowing that the lymphoid population is of T cell origin suggests that the patient has a reactive infiltrate rather than a malignant infiltrate. If this assay had been clinically available in both of these unusual cases, the results of the simple study in Example 1 would justify further expense of additional evaluation. The results of Example 3 justify not performing flow cytometry and proceeding to treatment for meningitis. Other applications of these kinds of analysis can be useful in other kinds of tumors such as MN/CA9 screening for cervical cancer, identifying specific tumor types in malignant infiltrates such as melanoma (using markers such as HMB-45), or identifying micrometastic disease in lymph nodes and bone marrows. In addition, single parameter analysis can be used in genetic phenotypic and genotypic analysis. For example, a peripheral blood sample can be permeabilized and treated with a specific probe to the bcr-abl translocation. The probe can be labeled with paramagnetic submicroscopic microspheres. The cells can then be treated with large, magnetic beads to identify the presence of the translocation that would be diagnostic of chronic myelogenous leukemia. Alternatively, a similar method can be used to identify the presence of intracellular proteins or RNA sequences using appropriate antibodies or nucleotide sequences, for example, the expression of the intracellular protein terminal deoxyribonucleotidyl transferase (TdT) using an antibody also labeled with paramagnetic microspheres and detecting the reaction using large surface magnetic beads. Finally, the use of CD64 expression has been proposed as a rapid diagnostic test for clinically significant acute inflammatory reaction (Lab. Hematol. 1995; 1:3–12). For reasons described above, flow cytometry is too expensive and difficult to use as a screening procedure for common conditions. The invented method allows rapid, inexpensive single parameter analysis for CD64 expression in peripheral granulocytes.

2) Simultaneous single parameter analysis is where there is simultaneous analysis of markers that are independent of each other. Most commonly, this is used in a B cell lymphoid population to determine expression of either kappa or lambda light chain restriction by expressed surface immunoglobulins. This can either be done by using similar beads as used in two separate glass slides analyzed simultaneously or by using a single slide using two sets of beads which can be easily distinguished based on size, color, or both. This is extremely useful as an inexpensive, rapid screen for B cell monoclonality. Other useful types of simultaneous single parameter analysis are in the setting of a malignant tumor of unknown origin where a cell suspension can be analyzed, either by using multiple separate slides or a single slide containing multiple sets of beads that can be distinguished by size, color, or both. In this example, these sets of beads typically include beads marking for CD45 (leukocyte common antigen), HMB-45 (melanoma), and a general cytokeratin marker (often AE1 and AE3 cocktail for epithelial tumors). A third type of this kind of analysis is to screen a population of lymphocytes to determine whether this population is composed of B cells, T cells, other cells, or any combination of these types.

3) The invention also includes multiparameter analysis where expression of markers are analyzed in conjunction with other markers. A simple, but common, example of this kind of analysis is depicted in Example 2 below. In Example 2, the positive binding reaction by the anti-CD20 coated beads which isolates the B cells is linked to kappa or lambda light chain expression. Multiparameter analysis enhances analysis since correctly identifying certain cell populations requires logical association of multiple subsets of markers. A case of acute leukemia serves as a useful example of this kind of analysis. Morphologic examination is one of the best methods for identifying the abnormal blast cells, but it does not characterize the kind of blasts present. Combining morphologic analysis with the present invention would yield the following typical kind of analysis. Anti-CD34 coated beads are combined with anti-HLA-DR coated beads to confirm expression of both of these markers in the malignant cell population. Positive expression of both of these markers supports the diagnosis of acute leukemia. The cells can then be analyzed with anti-CD13 and anti-CD33 coated beads in conjunction with anti-CD19 and anti-CD2 coated beads to determine if the cells are myeloid or lymphoid in origin. If they bind to CD13, CD33, or both, this confirms the myeloid derivation of the cells. The cells can also be analyzed with anti-CD15, anti-CD14, anti-CD56, anti-CD7, and anti-CD4 to determine subtype (myeloid, monocytic, or both) and to yield prognostic information. Of particular interest is successful analysis of acute promyelocytic leukemia (FAB subtype M3). Analysis of this tumor type by flow cytometry is fraught with errors and the tumor can be missed since it is composed of maturing myeloid cells. Using the present invention, morphologic analysis would confirm the presence of excess numbers of promyelocytic cells. In addition, the promyelocytes would usually be HLA-DR negative and could also be analyzed for the translocation of chromosomes 15 and 17 (t(15;17)) which is diagnostic of the disease. This kind of analysis is particularly useful in the microgranular variant of the disease in which the cells may resemble monoblasts. Monocytic leukemias can also be analyzed for additional monocytic markers such as CD36. Similar kinds of analyses can be performed for other hematologic malignancies, other tumor types, and other specific cell populations. In addition, the method can be used in reverse to offer a diagnostic test for myelodysplasia. Normal myeloid cells strongly bind the myeloid markers CD11b, CD13, CD16, and CD33. Among the changes seen in myelodysplasia, is decreased expression of these markers by flow cytometry. However, degenerating cells, as occurs in excessive sample age, temperature extremes, or other forms of specimen mishandling also causes decreased expression of these markers. Since morphologic correlation with flow cytometry is so poor, this form of analysis has not gained significant clinical acceptance since flow cytometry cannot reliably distinguish between degenerated normal cells and myelodysplastic cells. In the invented method there is excellent morphologic correlation, and trained observers will easily recognize degenerated cells. Therefore, normal cells can easily be distinguished from dysplastic cells, as normal cells will avidly bind beads coated with antibodies to these markers and dysplastic cells will not.

Another similar application can be used for analysis of breast cancer to determine prognostic factors such as Her2/ neu overexpression. Current state of the art utilizes primarily immunohistochemistry to localize actual tumor from surrounding breast tissue by visual methods. Her2/neu cytoplasmic membrane expression is estimated by the observer visually on a scale expressed as 0+ positive (no expression) to 4+ positive (strongest possible expression). There are semi-automated methods using image analysis that objectively measure Her2/neu staining but these are expensive and have limited availability. Alternatively, Her2/neu expression can be more objectively estimated by using fluorescent in-situ hybridization (FISH) which labels each gene copy with a fluorescent dot. The number of gene copies in each cell can be estimated by merely counting the dots within the nucleus of each cell. However, because cells cannot be easily counter-stained and observed, it is difficult to tell a malignant breast epithelial cell from an admixed benign one or even a stromal cell from the breast supporting matrix. Therefore, analysis by FISH has less acceptance in the clinical setting. More recently, Her2/neu expression can be performed by flow cytometry, however, like FISH there is no method for evaluating whether the analyzed cell is a malignant cell or a benign one. Using multiparameter analysis as described in the present invention, epithelial cells in a cell suspension can be distinguished from stromal cells by using large (10 micron) beads coated with anti-cytokeratin antibodies. Only epithelial cells would bind to this bead. Small 5 micron beads coated with an appropriate anti-Her2/ neu antibody is then added to the mixture and the suspension filtered. Her2/neu expression can be analyzed objectively by several methods. In one method, the filter itself can be analyzed to determine the quantity of 5 micron beads present on the filter by using methods such as fluorescence (if the 5 micron beads are fluorescent), electrostatic assessment, or other of a variety of known counting methods. In an alternative method, the suspension is transferred to a glass slide after filtration and the slide stained. Benign cells can be distinguished from malignant ones by morphologic assessment and the average number of beads binding to malignant cells can be estimated. This can either be performed manually by the observer or in a semi-automated manner using an electronic visual analysis to count the number of beads bound to each cell identified by the observer as malignant.

4) Signal amplification of weakly expressed antigens. One of the major advantages of flow cytometry is its ability to detect weakly expressed antigens on the surface of cells. Many antigens fall under this category and cannot be easily detected using alternative means such as routine immunostains using standard colorimetric detection methods such as diaminobenzadine (DAB). This problem in immunostains has been partially overcome using signal amplification methods such as tyramide signal amplification which is commercially available such as the Catalyzed Signal Amplification kit (Dako Corp., Carpinteria, Calif.). In the method, the primary antibody is conjugated to peroxidase enzyme (usually horseradish peroxidase or HRP) and oxygen free radicals are generated. In the presence of tyramide, the tyramide molecules themselves become free radicals and are short lived, highly reactive species. They readily conjugate to nearby molecules and are fixed in the immediate area of the primary antibody. The signal amplification derives from the ease in which tyramide is conjugate either to a fluorescent molecule or peroxidase. This added peroxidase is used to generate additional DAB signal and thus the signal is amplified. This signal amplification technique can also be applied to the invented method described herein. In one example, primary antibodies are conjugated to HRP to generate biotinylated tryamide free radicals as per the manufacturer's directions. Avidinated beads then readily and spontaneously bind to the cell surface at the appropriate sites. An alternative method uses submicroscopic beads that are invisible by routine light microscopy which are coated with the antibody of interest that also have a peroxide free radical generator such as HRP bound either to the antibody or to the surface of the bead. Biotinylated tyramide free radicals are generated as per the manufacturer's directions and then the cells are washed (or filtered) and treated with avidinated large beads that are easily visible by light microscopy (typically beads in the 5–20 micron size range). This method of signal amplification greatly enhances otherwise weak binding of beads when only rare antigens are present on the cell surface. Single amplification can also be achieved using (1) the dual-labelled Envision polymer system available from Dako Corp., Carpinteria, Calif. or (2) the mirror image complimentary antibodies technique, a kit for which is available from The Binding Site Company, Birmingham, England.

5) An alternative method of multiparameter analysis can be performed by first using a single set of beads to isolate the target cell population. The second parameter can then be detected by using routine or conventional immunohistochemical techniques such as immunoflouresence, colorometric methods such as peroxide reduced DAB or alkaline phosphatase methods, or immunogold/silver enhancement. This second antibody detection system can be applied either in the cell suspension or after the slide is made but before it is stained. The choice of method and detection method would be dependent on the desired stain in the final product and the particular antibody to be used. Since this method bypasses fixation and processing used in paraffin embedded tissue sections, antibodies that cannot be used in these paraffin can be used here such as CD10, CD2, or CD19.

6) Cell-bead binding is potentiated by the use of one or more enhancement reagents. In a preferred application, albumin, preferably 22% bovine albumin (Ortho Diagnostics, Raritan, N.J.) is added as an enhancement reagent to the cell suspension prior to the addition of beads. Albumin not only enhances reactions, it stabilizes cells and preserves cells during the remainder of the procedure. Other enhancement reagents can less preferably be used, such as various molecular weights of polyethylene glycol (PEG). PEG of a wide range of molecular weights and subgroup attachments can be used, but PEG 200 through PEG 3350 (PEG with molecular weights of 200 kD through 3350 kD) are preferred. Other antigen-antibody enhancement reagents such as low ionic strength salt solutions may also be used. When albumin or PEG solutions are used, an amount equal to approximately 5–20% w/v should be added to the cell suspension.

7) In order to reduce the possibility of granulocytes in cell suspensions from recognizing beads as foreign bodies and phagocytozing beads, a very low concentration (1 or 2 drops/ml) of any of a variety of fixatives may be added to the cell suspension. The preferred fixative for this application is ethanol, but formaldehyde, paraformaldehyde, methanol or glutaraldehyde are among the many commercially available fixatives that can be used for this purpose. If such fixatives are added, the cell suspension should be washed using a suitable cell suspension medium prior to adding beads. Failure to do so will inhibit binding of beads to cells. An alternate method of inhibiting this non-specific phagocytosis is a specific inhibitor of this particular cell function. These compounds act without causing cell death and may be useful in specific settings where preservation of cellular activity is desired. An example of this class of reagent is colchicine, which inhibits cytoplasmic microtubule formation. This inhibition blocks phagocytosis.

8) In situations where cell analysis cannot be performed within several hours of obtaining the sample, the cell suspension can be easily preserved for later analysis. The sample is simply added to approximately an equal volume of fixative, preferably a non-crosslinking fixative such as methanol or ethanol. A suitable commercially available fixative for such a purpose is Cytolite (Cytyc Corp., Boxborough, Mass.). Cross-linking fixatives such as formaldehyde or glutaraldehyde may also be used but this will limit the range of available antigens that can be analyzed. Cells preserved in this manner may be refrigerated for up to 10 days. In order to analyze the sample, it must be washed three times in a suitable buffer such as PBS with albumin. Analysis of the sample may then proceed as described above.

9) A specific cell type in a cell suspension may be quantitated using the following technique:
   a) An absolute cell count per unit volume is obtained by an independent method. This can be done manually using a hemocytometer but a commercially available cell counter is the preferred method.
   b) A specific quantity of the cell suspension, for example 1 ml, is used for the reaction. Therefore, a known total number of cells is used in the analysis.
   c) Beads coated with specific binding agents are added to the suspension and allowed to react, i.e., bind to cells of interest to form complexes.
   d) Filter out the complexes and place them on a glass slide and stain them.
   e) Relative percentages of each cell type is then estimated by counting the number of cells on each specific bead type.
   f) These percentages are used to calculate absolute numbers of cell populations per unit volume in the original cell suspension.

Using this approach, at least two different kinds of analysis can be accomplished. First, an analysis can be done where the total cell count equals A and cell count B plus cell count C approximately equals cell count A. Second, an analysis can be done where the total cell count equals A and there is a subset of A which is cell count D.

EXAMPLE

The physician needs an estimation of the absolute count of the CD4+ lymphocytes in a peripheral blood sample. The peripheral blood sample is analyzed with a hematology cell counter to obtain an absolute count of lymphocytes/ml in the peripheral blood. Four different bead populations are coated with anti-CD20, anti-CD3, anti-CD4, and anti-CD8 antibodies, respectively, and are added to the suspension. These four different bead types or sets can be distinguished from each other by size, color, or both. For convenience, these sets of beads are preferably split into two separate analyses: a first tube for CD20 and CD3 positive cells and a second tube containing large CD3 beads and small CD4 and CD8 beads. To the first tube, two different bead sets are added, one for CD20 and another for CD3. A specific quantity of peripheral blood sample such as 0.5 ml is added to the tube. Incubation and filtration (or separation) as described above is performed and one or more slides are prepared. From the first slide containing CD20 and CD3 cells, the relative percentages of B versus T cells can be estimated because the beads are a different color or a different size. From these percentages the absolute numbers of these cells per unit volume in the original sample can be calculated, and the two added together should almost equal the total absolute lymphocyte count (this can serve as a control). To the second tube, three different types of beads are added, a large bead for CD3, a first small bead for CD4 and a different small bead for CD8. Processing proceeds as described above. From the second tube the relative percentages of CD4+ lymphocytes versus CD8+ lymphocytes can be calculated and the absolute number of each obtained. This method eliminates the problems of interfering monocytes (which are also CD4 positive) which has to be corrected for in flow cytometry since using the proper filter size, they would not be present on the final slide. Even if they are on the final slide, they can be ignored because the CD3 beads are not bound to them.

Alternatively, an absolute count may show 200 Type A cells per unit volume. Beads Y and Z are added. Bead Y binds all Type A cells; bead Z binds Type D cells, which is a subset of Type A cells. After separating the complexes, examination shows one Type D cell for every ten Type A cells. This then calculates to an absolute count of 20 Type D cells per unit volume.

In the various cases mentioned above, a second or smaller or different bead is added to a tube or suspension to act as a marker. Optionally, instead of a second or smaller or different bead, one can instead use a non-bead marker such as a DNA or RNA probe, an immunohistochemical marker or a cytochemical stain. For example it is possible to quantitate the number of malignant cells in a case of follicular lymphoma in a peripheral blood or bone marrow sample. In this example, the number of lymphocytes is quantitated (in this example, 200 lymphocytes per ml) using an automated hematology analyzer. CD20 positive fluorescent beads and non-fluorescent CD3 beads are added to the suspension that are distinguishable from each other by size as well. Under routine light microscopy, the relative percentages of B cells and T cells is determined, for example, 25% B cells and 75% T cells. The absolute number of B-cells is then calculated by multiplying the relative percentage of B-cells (25%) by the absolute number of lymphocytes (200 per ml) to yield 50 B cells per ml. The slide is then treated by fluorescent in-situ hybridization for the IgH-bcl-2 gene rearrangement (t(14;18)) that is a marker of follicular lymphoma. This method is readily available from several commercial manufacturers such as Vysis, Inc. (Downers Grove, Ill.). Using a fluorescent microscope, the number of B-cells (as identified by the fluorescent bead) that co-expresses the in-situ fluorescent signal is counted and the relative percentage vs. the negative signal cells is determined. For example, of the B cells, it is noted that 1 in 5 (ie, 20%) co-express the in-situ fluorescent signal. Therefore, it is calculated that 20% of the 50 B cells per ml is malignant, ie, 10 follicular lymphoma cells per ml. Many variations of this method are possible using routine histochemical, cytochemical, immunohistochemical, and fluorescent markers.

10) The invention may also be used to prepare a cell suspension (rather than glass slides) that is enriched for the target cell suspension. In this variation, rather than transferring the cell-bead complexes to a slide for visual or other analysis, the filter may be gently washed to resuspend the cell-bead complexes. The filter (or variations described herein) may be rinsed either by reversing the fluid flow through the filter using clean buffer or by simply rinsing the filter in a suitable buffer. The cell-bead complexes can then be used for other purposes or reanalyzed by other methods. If the appropriate linker molecules as known in the art are used to attach the antibodies to beads, these linkers may be broken using chemical methods as known in the art such as enzymes. This will release the cells from the beads and make them available for other studies such as tissue cultures. Optionally one may use these cells for clinical uses as well. For example, a bone marrow or peripheral blood sample may be treated with anti-CD34 beads in which the anti-CD34 antibodies are bound to the beads using a reversible or cleavable bond. The CD34+ stem cells are then trapped on the filter and the filter is then washed using a suitable buffer. The stem cells are then released from the beads by cleaving the bonds holding the anti-CD34 antibody to the bead. The cells can then be separated from the beads again by filtration using appropriately sized beads and filter pores. For example, the beads can be 10 micron in diameter and a filter set at 7 microns can be used. This will trap the now unbound beads on the filter and the stem cells will pass through the filter.

The following Examples further illustrate various aspects of the invention, including single parameter and multiparameter analysis.

Example 1

A 30 year old man presented with pancytopenia and splenomegaly. Examination of the peripheral smear confirmed the pancytopenia. In addition, scattered cells were present that showed bland cytological characteristics, with a monocytoid appearance. The nuclei of these cells were round to oval, with a single intermediate nucleolus. There was abundant blue-gray cytoplasm that showed numerous cytoplasmic projections. A bone marrow examination revealed a hypocellular aspirate with similar cells present. Small clusters of abnormal cells were present on the core biopsy. A buffy coat sample of the peripheral smear was suspended in anti-CD20 coated 10-micron colorless beads to distinguish the abnormal cells from monocytes. The suspension was passed through an appropriate filter and the cells were then transferred to a glass slide and stained. A schematic of the resulting slide preparation is demonstrated in FIG. 2. Positive binding of the abnormal cell population to the 10-micron beads was a suspicious finding and suggested an abnormal B cell population. Flow cytometry performed on the bone marrow aspirate revealed a monoclonal population of monocytoid B cells expressing CD19, CD11c, CD103, and kappa light chain restriction confirming the diagnosis of hairy cell leukemia.

Example 2

A 68 year old man with a known history of chronic lymphocytic leukemia (CLL) presented for routine follow up examination. Clinical examination revealed that the patient had a peripheral white cell count of 435,500 cells/ml (normal range 4,300–11,000 cells/ml) which included 87% lymphocytes. Morphologic examination of the peripheral blood smear revealed predominantly an abnormal population of small lymphocytes with a small but significant population of large transformed cells. A suspension of cells in a liquid medium was provided. This sample was analyzed using anti-CD20 coated 10-micron beads, anti-kappa coated colorless 5-micron beads and anti-lambda coated colorless 5-micron beads in two separate tubes. In the procedure, the same sample was placed into each of 2 tubes. To each tube was added anti-CD20 coated 10-micron beads. These strongly bound the B cells. The question then was whether the B cells were kappa, lambda or a combination of both. Therefore, the 5 micron anti-kappa beads were added to the first tube and the 5 micron anti-lambda beads were added to the second tube. The results were then analyzed after filtering and placing on a glass slide. The cells strongly bound to the 10-micron beads and showed no binding to the anti-lambda beads and scattered binding to the anti-kappa beads (ie, like FIG. 3, except only 1–2 small beads per complex). These results are typical of CLL since this tumor strongly expresses CD20 but weak light chain restriction when analyzed by flow cytometry. As an alternative procedure, the 5 micron anti-kappa beads could be red and the 5 micron anti-lambda beads could be blue. The procedure could still be in 2 tubes as described above, or the kappa and lambda beads could be added simultaneously to the first tube. Analysis of this latter result would show a complex like FIG. 3 with blue only around the periphery (indicating monoclonal lambda), red only around the periphery (indicating monoclonal kappa), or a combination of red and blue around the periphery (indicating polyclonal B cells).

Example 3

A 19 year old man presented with headache and stiff neck to the emergency. His evaluation included obtaining a sample of cerebral spinal fluid for which emergency pathologist evaluation of the fluid was requested to rule out the presence of "blasts". Evaluation showed a relatively uniform population of small lymphocytes, and a diagnosis of viral meningitis was suggested. The patient's physician requested flow cytometry to completely rule out the possibility of malignancy. Since excess fluid was available, a small sample was treated with anti-CD20 coated 10-micron beads and anti-kappa and anti-lambda coated 5-micron beads in two separate tubes using essentially the same procedure as described in Example 2 above. The majority of cells did not bind to either the anti-CD20, anti-kappa, or anti-lambda beads, suggesting that the lymphoid population was composed predominantly of T cells. Flow cytometric analysis received two days later confirmed approximately 60% T cells and 40% B cells with normal T cell subsets and polytypic B cells consistent with viral meningitis.

A major advantage of the invention is that analysis of cell populations can now be performed by simple inspection of the glass slide by any physician or technologist. This kind of analysis can be used on any type of cell population bearing specific cell surface markers and in a wide variety of conditions (lymphoma is one example). Malignant clones from patients with acute leukemia can be similarly analyzed (using different types of markers), as can cell populations from patients with acquired immune deficiency syndrome. Finally, as tumor markers for solid neoplasms become available, this kind of analysis can also be performed in a similar fashion. For example, the new MN/CA9 antibody appears to be specifically expressed by dysplastic and malignant uterine cervical squamous cells. Since these cells may be suspended in a sea of normal cells, they may be difficult to identify even by routine immunohistochemistry. This method of analysis may both identify these cells and enrich a cytological preparation for them so that they can be more easily analyzed.

The present invention also provides a kit for practicing the invention. The kit contains one or more sets of beads as described above. Each set of beads is preferably in a container such as a sealed test tube. In some cases of simultaneous single parameter or multiparameter analysis, two or more sets of beads can be premixed, but typically they are kept separated. The kit also preferably contains one or more appropriate filters as described above and preferably a set of instructions.

Figure 4:
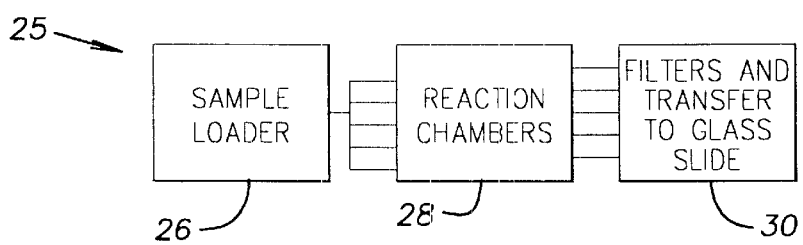
FIG. 4 is a schematic illustration of an automated device for performing phenotypic or immunophenotypic analysis in accordance with the present invention.
Figure 5:
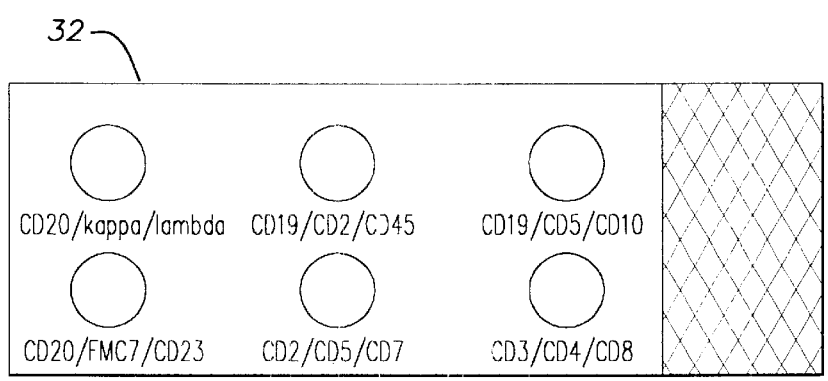
FIG. 5. is a schematic illustration of a single slide for use with the automated device of FIG. 4.

The methodology described herein can be automated and condensed. An example of a semiautomated device 25 for the performance of this kind of analysis is depicted in FIG. 4. A sample is prepared to make a cell suspension. The sample is then loaded into the machine 25 in the sample loader 26 and the machine 25 is programmed for the kind of analysis desired (lymphoma screen, acute leukemia analysis, myelodysplasia, etc.). The sample is divided into the appropriate number of reaction chambers 28 (for example, 2, 4, 6, 8, 10 or 12) and a preprogrammed number of bead sets (for example, 1, 2, 3, 4, etc. bead sets) added sequentially or simultaneously to each reaction chamber. The beads are incubated in the cell suspension and allowed to bind to the cells and all reaction chamber samples are then transferred to a filtration chamber 30 where each reaction chamber sample is filtered. The resulting filters or filtered materials are arranged so that all of them are simultaneously transferred to a single glass slide such as glass slide 32. The resulting slide contains a series of wells, each well corresponding to a reaction chamber sample. The multi-well slide can be stained, then scanned under a microscope. Each well can correspond to a multiparameter analysis, which is performed in minutes. FIG. 5 is a schematic for a suggested lymphoma panel slide using such a procedure. FIG. 5 shows 6 wells, each having run a 3-bead set as shown for multi-parameter analysis. In the upper left hand corner is "CD20/kappa/lambda". This indicates a well where the machine ran the CD20/kappa/lambda analysis described earlier herein. The other 5 wells give antibody information for running similar analyses as known in the art. Optionally a fourth or fifth set of beads can be added for further levels of analysis. Preferably after the single parameter or multiparameter incubation and filtration is carried out, the resulting complexes (such as in FIG. 3) are stained by immunohistochemistry or in-situ hybridization and then evaluated. Coated glass slides are preferred, to increase adhesiveness. Preferably, the slides are stained, coverslipped and examined by routine light microscopy to assess binding. Cells bound to beads are preferably assessed to characterize and ensure cell type.

In the present invention cells in suspension in fixative or tissue media can be phenotyped by antibody coated beads and isolated from the surrounding milieu by the use of a filter of proper pore size. These bound cells, thus separated from the sea of other cells, can be transferred to a glass slide and stained with a variety of stains for visualization. In addition, if immunophenotyping is not desired, a routine cytologic preparation using a variety of methods such as cytospin, cell block, or ThinPrep can be prepared.

Single parameter analysis can be used to phenotype cells of interest, such as enumerating relative numbers of kappa and lambda-bearing B lymphocytes. Another application is the isolation of MN/CA9 positive cervical epithelial cells.

Certain cell surface markers can be semi-quantitated by first isolating cells of interest and then enumerating the average number of beads bound to the surface.

It should be evident that this disclosure is by way of example and that various changes may be made by adding, modifying or eliminating details without departing from the fair scope of the teaching contained in this disclosure. The invention is therefore not limited to particular details of this disclosure except to the extent that the following claims are necessarily so limited.

What is claimed is:

1. A method of processing cells comprising the steps of:
   a) providing a suspension of cells in a liquid medium, said cells including first cells,
   b) contacting a group of first beads with said suspension, each of said first beads being coated with a binding substance or being magnetic such that each first bead is specifically adapted to bind to at least one of said first cells,
   c) incubating said first beads with said suspension for a period of time effective to permit said first cells to bind to said first beads to form first bead-first cell complexes, each first bead-first cell complex comprising a first bead and a first cell,
   d) separating said first bead-first cell complexes from said suspension by filtration through a filter, wherein said filter permits effective separation of said first bead-first cell complexes from said suspension, and
   e) examining said separated first bead-first cell complexes and characterizing said first cells, said method further comprising the step of adding to a preparatory suspension of said cells a fixative in an amount effective to inhibit phagocytosis of beads and subsequently washing out said fixative prior to said contacting in step (b).

2. The method of claim 1, wherein said fixative is selected from the group consisting of ethanol, formaldehyde, paraformaldehyde, methanol, glutaraldehyde and mixtures thereof.

3. The method of claim 1, wherein said suspension of cells includes second cells, said second cells and said first cells being in groups which do not overlap, said method further comprising the steps of:

1) prior to said filtration step, adding to said suspension a group of substantially identical second beads, each of said second beads being coated with a binding substance or being magnetic such that each second bead is specifically adapted to bind to a second cell, 2) incubating said second beads with said suspension for a period of time effective to permit said second cells to bind to said second beads to form second bead-second cell complexes, and 3) simultaneously separating said second bead-second cell complexes and said first bead-first cell complexes from said suspension by filtration.

4. The method of claim 3, wherein said first beads and said second beads are visually distinguishable in size or color.

5. The method of claim 1, wherein said suspension of cells includes second cells which are a subset of said first cells, said method further comprising the steps of:

1) prior to said filtration step, adding to a suspension comprising said first beads and first cells a group of substantially identical second beads, each of said second beads being coated with a binding substance or being magnetic such that each second bead is specifically adapted to bind to a second cell, said first beads being distinguishable from said second beads, 2) incubating said second beads with the suspension for a period of time effective to permit said second beads to bind to said second cells to form first bead-second cell-second bead complexes, each first bead-second cell-second bead complex comprising a first bead, a second cell, and a second bead, and 3) separating said first bead-second call-second bead complexes from said suspension by filtration.

6. The method of claim 1, said first beads have a diameter of at least 2 microns but not more than 30 microns.

7. The method of claim 1, comprising the step of transferring to a glass slide the bead-cell complexes separated by said filtration.

8. The method of claim 1, wherein said binding substance on said first beads comprises an antibody.

9. The method of claim 1, including a step of visually examining said separated first bead-first cell complexes and visually characterizing said first cells.

10. The method of claim 1, wherein said first beads are plastic microspheres.

11. The method of claim 1, wherein said fixative is ethanol.

12. A method of processing cells comprising the steps of:

a) providing a suspension of cells in a liquid medium, said cells including first cells b) contacting a group of first beads with said suspension, each of said first beads being coated with a binding substance or being magnetic such that each first bead is specifically adapted to bind to at least one of said first cells, c) incubating said first beads with said suspension for a period of time effective to permit said first cells to bind to said first beads to form first bead-first cell complexes, each first bead-first cell complex comprising a first bead and a first cell, d) separating said first bead-first cell complexes from said suspension by filtration through a filter, wherein said filter permits effective separation of said first bead-first cell complexes from said suspension, and e) examining said separated first bead-first cell complexes and characterizing said first cells, said method further comprising the step of adding to a preparatory suspension of said cells a fixative in an amount effective to preserve said cells for later analysis and subsequently washing out said fixative prior to said contacting in step (b).

13. The method of claim 12, wherein said fixative is selected from the group consisting of non-crosslinking fixatives.

14. The method of claim 12, wherein said suspension of cells includes second cells, said second cells and said first cells being in groups which do not overlap, said method further comprising the steps of:

1) prior to said filtration step, adding to said suspension a group of substantially identical second beads, each of said second beads being coated with a binding substance or being magnetic such that each second bead is specifically adapted to bind to a second cell, 2) incubating said second beads with said suspension for a period of time effective to permit said second cells to bind to said second beads to form second bead-second cell complexes, and 3) simultaneously separating said second bead-second cell complexes and said first bead-first cell complexes from said suspension by filtration.

15. The method of claim 14, wherein said first beads and said second beads are visually distinguishable in size or color.

16. The method of claim 12, wherein said suspension of cells includes second cells which are a subset of said first cells, said method further comprising the steps of:

1) prior to said filtration step, adding to a suspension comprising said first beads and first cells a group of substantially identical second beads, each of said second beads being coated with a binding substance or being magnetic such that each second bead is specifically adapted to bind to a second cell, said first beads being distinguishable from said second beads, 2) incubating said second beads with the suspension for a period of time effective to permit said second beads to bind to said second cells to form first bead-second cell-second bead complexes, each first bead-second cell-second bead complex comprising a first bead, a second cell, and a second bead, and 3) separating said first bead-second cell-second bead complexes from said suspension by filtration.

17. The method of claim 12, further comprising the step of:

a) prior to contacting the first beads with the suspension, permeabilizing said first cells and incubating said first cells wit paramagnetic microspheres which are bound to a reactive biomarker such that said reactive biomarker binds intracellularly in said first cell, and wherein each first bead is magnetic.

18. The method of claim 12, wherein said first beads have a diameter of at least 2 microns but not more than 30 microns.

19. The method of claim 12, further comprising the step of transferring to a glass slide the bead-cell complexes separated by said filtration.

20. The method of claim 12, wherein said fixative is selected from the group consisting of methanol and ethanol.

* * * * *

UNITED STATES PATENT AND TRADEMARK OFFICE
CERTIFICATE OF CORRECTION

PATENT NO. : 6,682,940 B2
DATED : January 27, 2004
INVENTOR(S) : Dan A. Pankowsky It is certified that error appears in the above-identified patent and that said Letters Patent is hereby corrected as shown below:

Column 21,
Line 36, please replace "call-second" with -- cell-second --.
Line 41, please insert -- further -- so that claim 7 reads as follows:
-- The method of claim 1, further comprising the step of transferring to a glass slide the bead-cell complexes separated by said filtration. --

Column 22,
Line 54, please replace "wit" with -- with --.

Signed and Sealed this

Twenty-fifth Day of May, 2004

JON W. DUDAS
*Acting Director of the United States Patent and Trademark Office*